United States Patent [19]

Abraham et al.

[11] 4,020,157
[45] Apr. 26, 1977

[54] SHORTENED ANALOGS OF SOMATOSTATIN

[75] Inventors: Nedumparambil A. Abraham, Dollard Des Ormeaux; Hans U. Immer, Mt. Royal; Verner R. Nelson, Kirkland; Kazimir Sestanj, Pointe Claire, all of Canada

[73] Assignee: Ayerst McKenna and Harrison Ltd., Montreal, Canada

[22] Filed: July 8, 1975

[21] Appl. No.: 594,159

[52] U.S. Cl. .......................... 424/177; 260/112.5 S
[51] Int. Cl.² ............... A61K 37/00; C07C 103/52
[58] Field of Search ............................. 260/112.5 S

[56] References Cited

UNITED STATES PATENTS

| | | | |
|---|---|---|---|
| 3,904,594 | 9/1975 | Guillemin et al. | 260/112.5 S |
| 3,917,578 | 11/1975 | Immer et al. | 260/112.5 S |
| 3,917,581 | 11/1975 | Immer et al. | 260/112.5 S |

Primary Examiner—Lewis Gotts
Assistant Examiner—Reginald J. Suyat

Attorney, Agent, or Firm—Stephen Venetianer

[57] ABSTRACT

Compounds of the formula 1 or 1a

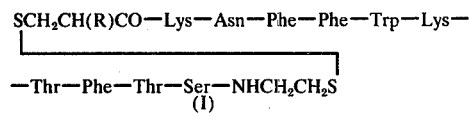

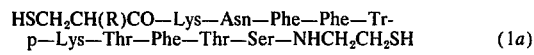

in which R is hydrogen or NHR$^1$ in which R$^1$ is lower aliphatic acyl containing from 1 – 6 carbon atoms or benzoyl, and pharmaceutically acceptable salts thereof are disclosed. The compounds of formulae 1 and 1a are useful for the management of diabetes and the treatment of acromegaly in mammals. Methods for their use also are disclosed.

36 Claims, No Drawings

SHORTENED ANALOGS OF SOMATOSTATIN

BACKGROUND OF THE INVENTION

1. Field of Invention

This invention relates to derivatives of the tetradecapeptide somatostatin. More particularly, this invention concerns shortened derivatives and salts thereof, a process for preparing said derivatives and salts, intermediates used in the process and methods for using the shortened derivatives and their salts.

2. Prior Art

The name "somatostatin" has been proposed for the factor found in hypothalamic extracts which inhibits the secretion of growth hormone (somatotropin). The structure of this factor has been elucidated by P. Brazeau et al., Science, 179, 77 (1973) and reported to have the following tetradecapeptide structure:

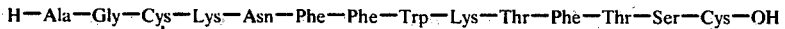

The abbreviations used herein for the various amino acids are Ala, alanine; Asn, asparagine; Cys, cysteine; Gly, glycine; Lys, lysine; Phe, phenylalanine; Ser, serine; Thr, threonine; and Trp, tryptophan.

The constitution of the tetradecapeptide somatostatin has been confirmed by synthesis; for example, see D. Sarantakis and W. A. McKinley, Biochem. Biophys. Res. Comm., 54 234 (1973), J. Rivier et al., Compt. Rend. Ser. D, 276, 2737 (1973) and H. U. Immer et al., Helv. Chim. Acta, 57, 730 (1974).

The important physiological activity of this tetradecapeptide established it as a compound of significance for clinical pharmacology relating to the treatment of acromegaly and the management of diabetes; for example, see K. Lundbaek et al., Lancet, 2, 131 (1970) and R. Guillemin in "Chemistry and Biology of Peptides", J. Meienhofer, Ed., 3rd American Peptide Symposium Boston 1972, Ann Arbor Science Publications, Ann Arbor, Mich., 1972.

The linear form of somatostatin, having two sulfhydryl groups instead of a disulfide bridge, has been prepared recently by J. E. F. Rivier, J. Amer. Chem. Soc., 96, 2986 (1974). He reports that the linear form is equipotent to somatostatin based on the ability of the two compounds to inhibit the rate of secretion of growth hormone by rat pituitary cells in monolayer tissue cultures.

Only recently have there been reported polypeptides, other than the natural hormone and its linear form having somatostatin-like activity. D. Sarantakis et al., Biochem. Biophys. Res. Comm., 55, 538 (1973) recently reported the synthesis of the somatostatin analog, [Ala$^{3,14}$]-somatostatin, by solid phase methods. This analog exhibited a very small amount of activity, about 0.01% of the potency of somatostatin. P. Brazeau et al., Biochem. Biophys. Res. Comm., 60, 1202 (1974) recently reported the synthesis of a number of acylated des-[Ala$^1$-Gly$^2$]-somatostatin derivatives by solid phase methods.

The present invention discloses shortened chain derivatives of somatostatin which show a level of activity greater than or of the same order as the natural hormone as well as a duration of activity which is greater than that of somatostatin. Those derivatives are prepared readily by a convenient process, which includes the following advantages: the process starts from readily available materials avoids noxious reagents, is executed facilely and utilizes easily removable protecting groups.

The foregoing advantages and attributes render the peptides of this invention useful for the management of diabetes and for the treatment of acromegaly.

SUMMARY OF THE INVENTION

The peptides of this invention are represented by formulae 1 and 1a; formula 1 representing the cyclic peptides of this invention and formula 1a representing the linear reduced form

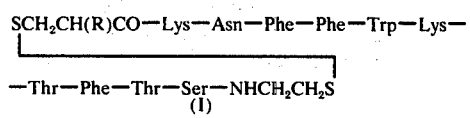

(1)

HSCH$_2$CH(R)CO-Lys-Asn-Phe-Phe-Trp-Lys-Thr-Phe-Thr-Ser-NHCH$_2$CH$_2$SH  (1a)

in which R is hydrogen or NHR$^1$ in which R$^1$ is lower aliphatic acyl having from 1 – 6 carbon atoms or benzoyl. The above peptides in which R is hydrogen are decapeptides, and those in which R is NHR$^1$ in which R$^1$ is as defined above are undecapeptides.

The pharmaceutically acceptable salts of the compounds of formula 1 and 1a are also included within the scope of this invention.

The peptides of this invention are prepared by a process which comprises: reacting according to the azide coupling method a first peptide hydrazide of the formula (2)

TrT—SCH$_2$CH(R)CO—Lys(Boc)—Asn—Phe—Phe—NHNH$_2$   (2)

in which R is as defined above with a second peptide of the formula (3)

H—Trp—Lys(Boc)—Thr(Bu$^+$)—Phe—Thr(Bu$^+$)—Ser(Bu$^+$)—NHCH$_2$CH$_2$S—Trt   (3)

to obtain the linear peptide of formula (4)

Trt—SCH$_2$CH(R)CO—Lys(Boc)—Asn—Phe—Phe—Trp—Lys(Boc—Thr(Bu$^+$)—Phe—Thr(Bu$^+$)—Ser(BU$^+$)—NHCH$_2$CH$_2$S—Trt   (4)

in which R is as defined herein; followed by oxidizing said linear peptide with iodine or thiocyanogen to obtain the corresponding cyclic disulfide derivative or formula (5)

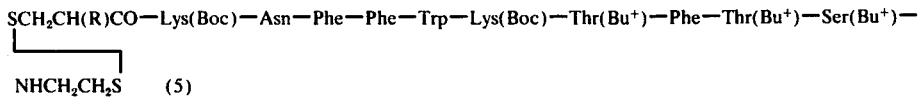
(5)

in which R is as defined here and subsequently removing all remaining protecting groups under moderately acidic conditions to obtain the corresponding peptide of formula 1; or followed by subjecting said linear peptide to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfydryl derivative by treatment with hydrogen sulfide, oxidizing said last-named derivative by treatment with oxygen, 1,2-diiodoethane, sodium or potassium fericyanide or iodine to obtain the corresponding cyclic disulfide derivative and removing the remaining protecting groups under moderately acidic conditions to obtain the desired peptide of formula 1. Alternatively, said cyclic disulfide derivative is reduced to said corresponding free disulfhydryl derivative by agents known to be effective for reducing known cyclic disulfides to their corresponding disulfhydryl derivatives.

A further aspect of this invention comprises the removal of all the protecting groups from the aforementioned linear peptide or the aforementioned disulfhydryl derivatives under moderately acidic conditions to obtain the linear reduced form of the peptide of this invention of formula 1a.

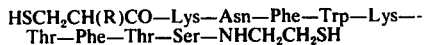

in which R is as defined herein.

The latter compound is also obtained by direct reduction of the cyclic peptide of formula 1 by agents known to be effective for reducing known cyclic disulfides to their corresponding disulfhydryl derivatives. If desired said reduced form of the cyclic peptide is converted to the corresponding derivative of formula 1 by one of the above oxidizing agents.

DETAILS OF THE INVENTION

In general the abbreviations used herein for designating the amino acids and the protective groups are based on recommendations of th IUPAC-IUB Commission on Biochemical Nomenclature, see Biochemistry, 11, 1726 – 1732 (1972). For instance, Cys, Lys, Asn, Phe, Trp, Thr, and Ser represent the "residues" of L-cysteine, L-lysine, L-asparagine, L-phenylalanine, L-tryptophan, L-threonine and L-serine, respectively. By the residue is meant a radical derived from the corresponding L-amino-acid by eliminating the OH portion of the carboxyl group and the H portion of the amino group. All the amino acids have the natural L-configuration.

A number of procedures of techniques for the preparation of peptides have hitherto been well established. For instance, the functional groups which are not involved in the peptide bond formation reaction are optionally protected by a protecting group or groups prior to the condensation reaction. For example, protecting groups which may be chosen for an amino function of a peptide or amino acid not involved in the peptide bond formation are: the alkoxycarbonyls which include benzyloxycarbonyl (represented by Z), +-butoxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycabonyl, isopropyloxycarbonyl, or ethoxycabonyl; the acyl type protecting groups which include formyl, trifluoroacetyl, phthalyl, acetyl (Ac), or toluenesulfonyl; the alkyl type protecting groups which include triphenylmethyl or trityl (represented by Trt) or benzyl; the preferred protecting groups and in the process of this invention are benzyloxycarbonyl, +-butoxycarbonyl, triphenylmethyl and α,α-dimethyl-3,5-dimethoxy-benzyloxycarbonyl. The protecting groups for the hydroxyl of serine and tyrosine are represented by acetyl, tosyl, benzoyl, tert-butyl (represented by Bu$^+$), trityl, and benzyl; the preferred protecting group is tert-butyl. The protecting groups on the sulfur of cysteine or modified cysteine are illustrated by benzyl, triphenylmethyl or trityl (represented by Trt), benzyloxycarbonyl, or acetamidomethyl (represented by Acm); the preferred protecting groups are trityl and acetamidomethyl. The carboxylic acid function of a peptide or amino acid can be considered protected by a lower alkyl or lower aralkyl ester which include methyl (represented by OMe), ethyl (represented by OE+), or benzyl (represented by OBzl); and also by substituted hydrazides which include +-butoxycarbonyl hydrazide (represented by NHNH Boc), benzyloxycarbonyl hydrazide (represented by NHNH Z), or α,α-dimethyl3,5-dimethoxybenzyloxycarbonyl hydrazide (represented by NHNH Ddz).

To promote facile condensation of the peptide carboxyl group with a free amino group of another peptide to form a new peptide bond the terminal carboxyl group must be activated. Descriptions of such carboxyl-activating groups are found in general textbooks of peptide chemistry; for example K. D. Kopple, "Peptides and Amino Acids", W. A. Benjamin, Inc., New York, 1966, pp. 45 – 51 and E. Schroder and K. Lubke, "The Peptides"; Vol. 1, Academic Press, New York, 1965, pp. 77 – 128. Examples of the activated form of the terminal carboxyl are acid chloride, anhydride, azide, activated ester, or o-acyl urea of a dialkylcarbodiimide. The following activated esters have proved to be particularly suitable in the process of this invention: 2,4,5-trichlorophenyl (represented by OTcp), pentachlorophenyl (represented by OPcp), p-nitrophenyl (represented by ONp), or 1-benzotriazolyl; the succinimido group is also useful for such activation.

The term "azide method" as used herein refers to the method of coupling two peptide fragments which comprises the reaction of a peptide hydrazide with a reagent which furnishes nitrous acid in situ. Suitable reagents for this purpose include organic nitrites (e.g. +-butyl nitrite, isoamyl nitrite) or alkali metal nitrite salts (e.g. sodium nitrite, potassium nitrite) in the presence of a strong acid such as hydrogen chloride or sulfuric or phosphoric acid. The corresponding peptide azide thus obtained is then reacted with a peptide having a free amino group to obtain the desired peptide.

Preferred conditions for the azide method of coupling comprises reacting the peptide hydrazide with nitrous acid, generated in situ from an organic nitrite in the presence of a strong acid, preferably hydrogen chloride, (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like at −30° to 20° C, preferably at about −15° C for 10 to 30 minutes to obtain the corresponding azide. The peptide azide can be isolated and crystallized and is preferably allowed to remain in the reaction mixture. Thereafter the azide in the above mixture is reacted with the peptide unit having the free amino group at temperatures ranging from −30° C to 20° C for about one to 2 hours and then at 0° to 30° C for 10 to 30 hours. An acid acceptor, preferably an organic base, for example N-ethyldiisopropylamine, N-ethylmorpholine or triethylamine, is present in the reaction mixture in order to make the reaction medium slightly alkaline, preferably pH 7.0 to 7.5. See also the above cited textbooks of Kopple or Schroder and lubke for additional descriptions of this method.

The terms "peptide, polypeptide, tripeptide, hexapeptide, and the like" as used herein are not limited to refer to the respective parent peptides but are also used with reference to modified peptides having functional or protecting groups. The term "peptide" as used herein is used with reference to a peptide with two to eleven amino acids residues. In addition the residue "$SCH_2CH(R)CO$" as used herein is used in reference to the residue of an acylated or benzoylated cysteine when R is $NHR^1$ in which $R^1$ is as defined above or to a modified residue of cysteine when R is H.

The abbreviation Me represents a methyl group and $NHNH_2$ represents a hydrazide group.

The term "lower alkyl" as used herein contemplates hydrocarbon radicals having one to three carbon atoms and includes methyl, ethyl and propyl.

The term lower "aliphatic acyl having from 1 − 6 carbon atoms" represent straight or branched chain acyl groups and includes formyl, acetyl, propionyl, butyryl, isobutyryl, pivaloyl, n-hexanoyl and the like.

The term "mineral acid" as used herein contemplates the strong inorganic acids and includes hydrochloric, hydrobromic, sulfuric, or phosphoric acid. When the terms is used in conjunction with an anhydrous system, anhydrous hydrogen chloride is the preferred mineral acid.

The term "mildlyacidic conditions" as used herein contemplates conditions in which a dilute aqueous solution of an organic acid, for example 30 − 80% aqueous formic, acetic or propionic acid, preferably 70 − 80%, or mixtures thereof, is a principal component of the reaction medium.

The term "moderately acidic conditions" as used herein contemplates conditions in which concentrated organic acids or solutions of the mineral acids are used as a principal component of the reaction medium at temperatures ranging from about −30° to 30° C. Examples of preferred conditions in this case include the use of 50 to 100% trifluoroacetic acid at 0° to 30° C or 0.1 − 12N hydrochloric acid in aqueous solution or in solution in an organic solvent, or hydrogen chloride in solution in anhydrous organic solvents at −20° to 10° C.

The term "organic nitrite" includes the commercially available alkyl nitrites, for instance, +-butyl nitrite, isoamyl nitrite, and the like.

The term "organic base" as used herein includes triethylamine, N-ethylmorpholine, N-ethyldiisopropylamine and the like.

The term "strong base" as used herein contemplates both organic bases as described above and strong inorganic bases including the hydroxides and carbonates of sodium and potassium.

The peptides of this invention, including the cyclic and the linear reduced forms thereof, are obtained in the form of the free base or an acid addition salt either directly from the process of this invention or by reacting the peptide with one or more equivalents of the appropriate acid. Examples of preferred salts are those with pharmaceutically acceptable organic acids, e.g. acetic, lactic, succinic, benzoic, salicylic, methanesulfonic or toluenesulfonic acid; as well as polymeric acids such as tannic acid or carboxymethyl cellulose, and salts with inorganic acids such as hydrohalic acids, e.g. hydrochloric acid, or sulfuric acid, or phosphoric acid. It should be noted that the peptides have two basic nitrogens giving rise to addition salts with one to possibly two equivalents of acid. If desired, a particular acid addition salt is converted into another acid addition salt, e.g., a salt with a non-toxic, pharmaceutically acceptable acid, by treatment with the appropriate ion exchange resin in the manner described by R. A. Boissonas et al., Helv. Chin, Acta, 43, 1349 (1960). Suitable ion exchange resins are cellulose based cation exchangers, for example carboxymethylcellulose or chemically modified, cross-linked dextran cation exchangers, for example, those of the Sephadex C type, and strongly basic anion exchange resins, for example those listed in J. P. Greenstein and M. Winitz "Chemistry of the Amino Acids", John Wiley and Sons, Inc., New York and London, 1961, Vol. 2, p. 1456.

The peptides produced by the process of this invention, as well as their corresponding pharmaceuticaliy acceptable salts, are useful because they possess the pharmacological activity of the natural tetradecapeptide somatostatin. Their activity is demonstrated readily in pharmacological tests such as a modification [A. V. Schally et al., Biochem. Biophys. Res. Commun., 52, 1314 (1973); J. Rivier et al., C. R. Acad. Sci. Paris, Ser. D, 276, 2737 (1973)] of the in vitro method of M. Saffran and A. V. Schally, Can. J. Biochem. Physiol., 33, 405 (1955).

The activity of the peptides of formula 1 or 1a of this invention is demonstrated also in vivo in a modification of the pentobarbital-induced increase in plasma growth hormone level in the rat as describes by Brazeau et al., cited above. In this test the peptides of this invention show a level of activity which is greater than or of the same order as somatostatin.

The peptides of this invention are useful for the treatment of acromegaly and related hypersecretory endocrine states and in the management of diabetes in mammals; see for example, P. Brazeau et al., cited above. When the peptides or salts thereof are employed for such treatment or management, they are administered systemically, preferably parenterally, in combination with a pharmaceutically acceptable liquid carrier. The peptides of formula 1 or 1a have a low order of toxicity. The proportion of the peptide or salt thereof is determined by its solubility in the given carrier, by the given carrier, or by the chosen route of administration. When the peptide of a salt thereof is used in a sterile aqueous solution, such solution may also contain other solutes such as buffers or preservatives, as well as sufficient pharmaceutically acceptable salts or glucose to make the solution isotonic. The dosage will vary with the form of administration and with the particular species to be treated and is preferably kept at a level of from 1 mcg to 300 mcg per kilogram body weight. However, a dosage level in the range of from about 1 mcg to about 50 mcg per kilogram body weight is most desirably employed in order to achieve effective results.

The peptides or salts thereof may also be administered in one of the long-acting, slow-release or depot dosage forms described below, preferably by intramuscular injection or by implantation. Such dosage forms are designed to release from about 0.1 mcg to about 50 mcg per kilogram body weight per day.

It is often desirable to administer the agent continuously over prolonged periods of time in long-acting, slow-release or depot dosage forms. Such dosage forms may either contain a pharmaceutically acceptable salt of the peptide having a low degree of solubility in body fluids, for example one of those salts described below, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example, zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton; Pennsylvania, 1970. Long-acting, slow-release preparation of the peptide produced according to the process of this invention may also be obtained by microencapsulation in a pharmaceutically acceptable coating, for example gelatine, polyvinyl alcohol or ethyl cellulose. Further examples of coating materials and of the processes used for microencapsulation are described by J. A. Herbit in "Encyclopedia of Chemical Technology", Vol. 13, 2nd Ed., Wiley, New York 1967, pp. 436–456. Such formulations, as well as suspensions of salts of the peptide which are only sparingly soluble in body fluids, for example salts with pamoic acid or tannic acid, are designed to release from about 1.0 mcg to about 100 mcg of the active compound per kilogram body weight per day, and preferably administered by intramuscular injection. Alternatively, some of the solid dosage forms listed above, for example certain sparingly water-soluble salts or dispersions in or adsorbates on solid carriers of salts of the peptide, for example dispersion in a neutral hydrogel of a polymer of ethylene glycol methacrylate or similar monomers cross-linked as described in U.S. Pat. No. 3,551,556 may be formulated in the form of pellets releasing about the same amounts as shown above and may be implanted subcutaneously or intramuscularly.

PROCESS

The process of this invention will be illustrated by the following embodiments in which specific peptides of formulae 1 and 1a are prepared.

a. Compounds 1 and 1a (R = NHR$^1$ in which R$^1$ is as defined above)

The requisite first peptide hydrazide of formula (2) Trt—SCH$_2$CH(R)CO—Asn—Phe—Phe—NHNH$_2$ in which R is NHR$^1$ in which R$^1$ is as defined above or alternatively written with formula (2a) as R$^1$—Cys(Trt)—Lys(Boc)—Asn—Phe—Phe—NHNH$_2$ is prepared by acylation of the pentapeptide of formula H—Cys(Trt)—Lys(Boc)—Asn—Phe—Phe—OMe to obtain the pentapeptide of formula R$^1$—Cys(Trt)—Lys(Boc)—Asn—Phe—Phe—OMe which is subjected to hydrazinolysis to obtain said first pentapeptide hydrazide.

In a preferred embodiment of the preparation of the above first pentapeptide hydrazide (2), a mixture of substantially equimolar amounts of an organic base, preferably N-ethylmorpholine, and the pentapeptide of formula H—Cys(Trt)—Lys(Boc)—Asn—Phe—Phe—OMe, prepared as described by H.U. Immer et al., cited above, in an inert organic solvent, preferably dimethylformamide or tetrahydrofuran, at about 0° to 10° C, is treated with an excess, preferably 1.1 to 2 molar equivalents, or the desired p-nitrophenyl acylate or benzoate, e.g. p-nitrophenyl acetate, prepared as described by F. D. Chattaway, J. Chem. Soc., 2495 (1931). The mixture is kept at 0° to 10° C for about 15 to 30 hours and evaporated. The residue is taken up in a polar organic solvent, preferably methanol, and slowly added to a non-polar organic solvent, preferably diethyl ether. The residue is collected and crystallized to obtain the corresponding acylated or benzolated pentapeptide, e.g. the pentapeptide of formula R$^1$-Cys(Trt)-Lye(Boc)-Asn-Phe-Phe-Ome in which R$^1$ is as defined above. Said last-named compound is dissolved in an inert organic solvent, for example methanol, ethanol, dimethylformamide, and the like, preferably methanol. The solution is treated with an excess of hydrazine hydrate, for example 15 to 30 molar equivalents. The reaction mixture is kept at about 0° to 10° C for about 40 to 60 hours. The precipitate is collected and dried to yield said first pentapeptide hydrazide of formula (2) or (2a) in which R$^1$ is as defined above, for example the pentapeptide hydrazide of formula (2) or (2a) in which R$^1$ is acetyl.

In the next step of the process of this invention the aforementioned first pentapeptide hydrazide (2) and a second viz., the hexapeptide of formula (3) H—Trp—Iys(Boc)—Thr(Bu$^+$—Phe—Thr(Bu$^+$)-Ser(Bu$^+$)—NHCH$_2$CH$_2$STrt (described in the co-pending U.S. patent application Ser. No. 493,595; filed Aug. 1, 1974) are coupled according to the azide coupling method to obtain the corresponding linear undecapeptide of formula (4) in which R is NHR$^1$ as defined above alternatively written with formula (4a) as R$^1$—Cys(Trt)—Lys—(Boc)—Asn—Phe—Phe—Trp—Lys(Boc)—Thr(Bu$^+$)—Phe—Thr(Bu$^+$)—Ser(Bu$^+$)—NHCH$_2$CH$_2$S—Trt, for example the linear undecapeptide of the above formula (4a) in which R$^1$ is acetyl.

A convenient and efficacious procedure for this step comprises dissolving the first pentapeptide hydrazide (2) in which R is NHR$^1$ wherein R$^1$ is as defined above in an organic solvent, preferably dimethylformamide and cooling the mixture to about −20° to −10° C. A solution of about two to five molar equivalents of a strong acid in an inert organic solvent, preferably three molar equivalents of hydrogen chloride in ethyl acetate, is added to the above solution, followed by 1.0 to 1.5 molar equivalents of an organic nitrite, for example, 1.2 molar equivalents of t-butyl nitrite. In this manner the corresponding pentapeptide azide of formula $R^1$ —Cys(Trt)—Lys(Boc)—Asn—Phe—Phe—$N_3$ in which $R^1$ is as defined above, for example, acetyl, is obtained. After about 10 to 20 minutes at about −20° to 0° C, a solution of substantially one molar equivalent of the above second hexapeptide and an organic base in an inert organic solvent, preferably two to four molar equivalents of N-ethyldiisopropylamine in dimethylformamide, cooled to about −20° to 0° C, is added to the above solution containing said azide. The reaction mixture is then stirred at about −20° to 0° C for one to two hours and then at about 20° to 30° C for 20 to 30 hours. The solvent is evaporated under reduced pressure. The residue is triturated with cold dilute aqueous citric acid, water, and methanol, and separation of the solid gives the aforementioned linear undecapeptide of formula (4) in which R is $NHR^1$ as defined above, alternatively written as formula (4a) in which $R^1$ is as defined above.

The aforementioned requisite second hexapeptide described in U.S. patent application Ser. No. 493,595 cited above is obtained readily by coupling according to the azide coupling method the hexapeptide hydrazide of formula Ddz—Trp—Lys(Boc)—Thr($Bu^+$)—Phe—Thr($Bu^+$)—Ser($Bu^+$)—$NHNH_2$, prepared as described by H. U. Immer et al., cited above, with 2-tritylthioethylamine to give the hexapeptide of formula Ddz-Trp-Lys-(Boc)-Thr($Bu^+$)-Ser($Bu^+$)-$NHCH_2CH_2STrt$. Treatment of the latter compound under mildly acidic conditions affords said second hexapeptide of formula (3).

The conversion of the preceding linear undercapeptide of formula (4) or (4a) obtained as described above in which $R^1$ is as defined above, for example acetyl, to the corresponding compound of formula 1 ($R = NHR^1$) is accomplished conveniently and efficiently by first subjecting the linear unecapeptide to the action of iodine, preferably in the presence of a lower alkanol or acetic acid, whereby removal of the sulfhydryl protecting groups, i.e. Trt, and concomitant formation of the disulfide bridge occurs to give the corresponding cyclic disulfide derivative of formula (5) in which R is $NHR^1$, alternatively written with formula (5a) as suitable lower alkanol, for example, propanol, isopropanol or butanol. This solution is added to an excess of iodine (5 to 25, preferably 10 molar equivalents) dissolved in a lower alkanol, preferably 2 - 5% iodine in methanol). The time and temperature of this reaction is not critical; however, it is desirable to keep the reaction between 0° and 30° C by regulating the addition to the iodine solution or by cooling of the reaction mixture, or by a combination of both. Under these conditions the addition usually takes 30 to 60 minutes. After the addition of iodine the mixture is stirred at 20° to 30° C for 30 to 120 minutes, preferably for 60 minutes. Thereafter the mixture is cooled to about 0° C and an excess of a mild reducing agent, preferably sodium thiosulfate in aqueous solution, is added in order to destroy excess iodine. The mixture is concentrated and the residue is suspended in water. Collection of the solid material affords the desired corresponding cyclic disulfide derivative of formula (5) in which R is $NHR^1$ and $R^1$ is as defined above, for example the compound of formula (5) in which R is $NHCOCH_3$ in which the Boc and $Bu^+$ protecting groups are still present.

Alternatively, the linear undecapeptide (4) is converted to the aforementioned corresponding cyclic disulfide (5) derivative by the method of R. G. Hiskey and R. L. Smith, J. Amer. Chem. Soc. 90, 2677 (1968) using thiocyanogen.

Again alternatively, the above cyclic disulfide derivative (5) is also obtained by selectively removing the sulfhydryl protecting groups of the above linear undecapeptide (4) by the action of a mercuric or silver salt, for example, mercuric acetate, mercuric chloride, silver acetate or silver nitrate, in an inert organic solvent, for example dimethylformamide or acetic acid, according to known methods; for example, see B. Kamber, and W. Rittel, Helv. Chem. Soc. 87, 4922 (1965) and R. G. Denkewalter et al., J. Amer. Chem. Soc., 91, 502 (1969). The corresponding mercuric or disilver salt is then converted by hydrogen sulfide treatment to the corresponding free disulfhydryl derivative, see L. Zervas et al., cited above. The latter derivative is then converted to the aforementioned cyclic disulfide derivative (5) by treatment with a mild oxidizing agent, for example iodine according to the method described hereinbefore, or oxygen according to the method of J. Rivier et al., C. R. Acad. Sci. Ser. D, 276, 2737 (1973), or 1,2-diiodoethane according to the method of F. Weygand and G. Zumach, Z. Naturforsch. 17b, 807 (1962), or sodium or potassium ferricyanide according to the method of D. Jarvis et al., J. Amer. Chem. Soc., 83, 4780 (1961).

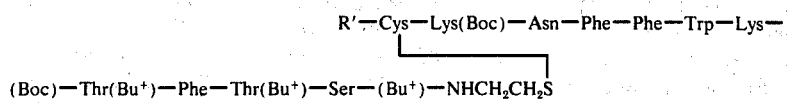

in which $R^1$ is as defined above, for example acetyl. Subsequent treatment of the latter compound under moderately acidic conditions removes the remaining protecting groups (i.e. Boc and $Bu^+$) to give the corresponding cyclic peptide of formula 1 in which R is $NHR^1$ in which $R^1$ is as described above, for example acetyl.

In a preferred embodiment of the above transformation the linear undecapeptide of formula (4) is dissolved in acetic acid or methanol, ethanol or other Finally, the aforementioned cyclic disulfide derivative of formula (5) in which R is $NHR^1$ and $R^1$ is as defined above, is transofrmed into the cyclic undecapeptide of formula 1 ($R = NHR^1$ and $R^1$ is as defined above) by subjecting the former to moderately acidic conditions whereby the remaining protecting groups of the cyclic disulfide derivative are removed. Generally this step is carried out by dissolving the cyclic disulfide derivative in an aqueous reaction medium containing a strong acid at 0° to 20° C for 10 to about 60 minutes. Examples of such media are 80 to 100% trifluoroacetic acid, 10 to 20% aqueous sulfuric acid, 10% phosphoric acid, 10–30% hydrobromic acid or 10 to 36% hydrochloric acid. An extremely useful medium is concentrated hydrochloric acid. Preferred conditions for this step include dissolving the cyclic disulfide in a minimum of concentrated hydrochloric acid cooled to 0° C and stirring the mixture at 0° C for five to ten minutes under a nitrogen atmosphere. Thereafter glacial acetic acid (10 vols.) is added, the solution is cooled to about −70° C and lyophilized to give the cyclic undecapeptide of formula 1 ($R = NHR^1$ and $R^1$ is as defined above), for example the compound of formula 1 in which R is $NHCOCH_3$. The latter product is purified further by ion exchange chromatography, preferably using a carboxymethyl cellulose cation exchanger and ammonium acetate as the eluant. In this case the peptide is obtained in the form of its acid addition salt with acetic acid. Alternatively, the peptide is purified by partition chromatography on a chemically modified cross-linked dextran; for example, Sephadex LH-20 or Sephadex G-25. In the case where Sephadex LH-20 is employed and methanol as the eluting solvent, the peptide is obtained in the form of its acid addition salt with hydrochloric acid. In the case where Saphadex G-25 and acetic acid or acetic acid-water-butanol is employed, the peptide is obtained in the form of its acetic acid addition salt. The latter salt, when subjected to repeated lyophilization from water yields the cyclic undecapeptide of formula 1 ($R = NHR^1$ and $R^1$ is as defined above), for example the cyclic disulfide of acetylcysteinyllysylasparaginylphenylalanylphenylalanyltryptophyllysylthreonylphenylalanylthreonylseryl-2-thioethylamide, in the form of the free base.

The linear reduced form of the cyclic undecapeptide of formula 1 ($R = NHR^1$ and $R^1$ is as defined above) is obtained preferentially by removal of the protecting groups from the aforementiond linear undecapeptide of formula (4) in which R is $NHR^1$ and $R^1$ is as defined above. Convenient conditions for this deprotection step comprise dissolving the linear undecapeptide (4) in concentrated hydrochloric acid at about 0°to 5° C in an inert atmosphere, for example, nitrogen or argon. The mixture is kept at this temperature for five to 10 minutes. Subsequent isolation of the linear reduced form ($1a$, $R = NHR^1$ and $R^1$ is as defined above) is accomplished in the same manner as described previously for the isolation of the cyclic undecapeptide (1; R = $NHR^1$ and $R^1$ is as defined above).

Also, the linear reduced form is obtained directly by reduction of the cyclic undecapeptide of formula 1 ($R=NHR^1$ and $R^1$ is as defined above). Reduction with dithiothreitol according to the method of W.W. Cleland, Biochem. 3, 480 (1964) is preferred, although other agents known to be effective for the reduction of cyclic disulfides to the corresponding disulfhydryl derivative are applicable, for example, sodium bisulfide followed by hydrolysis of the intermediate dithiosulfate derivative.

b. Compounds 1 and $1a$ (R = H)

The requisite first peptide hydrazide viz., the tetrapeptide of formula (2) $Trt—S—CH_2CH(R)CO—Lys(Boc)—Asn—Phe—Phe—NHNH_2$ in which R is hydrogen is prepared by reacting an activated ester of 3-tritylthiopropionic acid with a tetrapeptide of formula $H—Lys(Boc)—Asn—Phe—Phe—OMe$ to obtain the tetrapeptide of formula (2) in which R is hydrogen, viz., $Trt—SCH_2CH_2CO—Lys(Boc)—Asn—Phe—Phe—OMe$ which is subject to hydrazinolysis to obtain said first tetrapeptide hydrazide of formula (2) in which R is hydrogen.

In a preferred embodiment of the preparation of the above first tetrapeptide hydrazide, the activated ester of 3-tritylthiopropionic acid, preferably the pentachlorophenyl ester, is prepared by combining substantially equimolar amounts of 3-tritylthiopropionic acid, pentachlorophenol and dicyclohexylcarbodiimide in an inert organic solvent, preferably tetrahydrofuran, at about 0° to 10° C. The mixture is stirred at about 0° to 10° C for about 1 hour and then at about 20° to 30° C for about 1 hour. The mixture is cooled to about 0° C, filtered and the filtrate evaporated. The residue is crystallized to obtain 3-tritylthiopropionic acid pentachlorophenyl ester. A solution of said last-named compound and a substantially equimolar amount of the tetrapeptide of formula H-Lys(Boc)-Asn-Phe-Phe-OMe acetate, prepared as described by H. U. Immer et al., cited above, in an inert organic solvent, preferably dimethylformamide or tetrahydrofuran, is treated with a substantially equimolar amount of an organic base, preferably triethylamine, at about 20° to 30° C. The mixture is stirred for 2 to 3 days at about 20° to 30° C and the solvent evaporated under reduced pressure. The residue is triturated with cold dilute aqueous citric acid and water, dried, and crystallized to give the tetrapeptide of formula $Trt—SCH_2CH_2CO—Lys(Boc)—Asn—Phe—Phe—OMe$. Said last-named compound is dissolved in an inert organic solvent, for example, methanol, ethanol, or preferably dimethylformamide. The solution is treated with an excess of hydrazine hydrate, for example 15 to 30 molar equivalents. The reaction mixture is kept at about 20° to 30° C for about 20 to 30 hours and evaporated under reduced pressure. The residue is triturated with cold water and dried to give said tetrapeptide hydrazide of formula (2, R = H) $Trt—SCH_2CH_2CO—Lys(Boc)—Asn—Phe—Phe—NHNH_2$.

In the next step of the process of this invention the above first tetrapeptide hydrazide (2) and the second hexapeptide of formula (3) $H—Trp—Lys(Boc)—Thr(Bu^+)—Ser(Bu^+)—NHCH_2CH_2S—Trt$, described above in (a), are coupled according to the azide coupling method to obtain the corresponding linear decapeptide of formula (4) in which R is hydrogen, viz., the linear decapeptide $Trt—SCH_2CH_2CO—Lys(Boc)—Asn—Phe—Phe—Trp—Lys(Boc)—Thr(Bu^+)—Ser(Bu^+)—NHCH_2CH_2S—Trt$.

This coupling is conveniently achieved by dissolving the first tetrapeptide hydrazide (2) in an organic solvent, preferably a mixture of dimethyl sulfoxide and dimethylformamide, and cooling the mixture to about −30° to −15° C. A solution of about two to five molar equivalents of a strong acid, preferably three molar equivalents of hydrogen chloride in ethyl acetate, is added to the latter solution, followed by 1.0 to 1.5 molar equivalents of an organic nitrite, for example 1.2 molar equivalents of t-butyl nitrite. In this manner the corresponding tetrapeptide azide of formula $Trt—SCH_2CH_2CO—Lys(Boc)—Asn—Phe—Phe—N_3$ is obtained. After about 15 minutes at about −20° to 0° C a solution of substantially one molar equivalent of the second hexapeptide (3) and an organic base, preferably two to four molar equivalents of N-ethyldiisopropylamine, in an inert organic solvent, preferably dimethylformamide, cooled to about −20° to 0° C, is added to the above solution containing said azide. The reaction mixture is then stirred at about −20° to 0° C for one to two hours and then at about 20° to 30° C for about 20 to 30 hours and evaporated under reduced pressure. The residue is triturated with cold dilute aqueous citric acid, water, methanol and separation of the solid gives the aforementioned linear decapeptide (4, R = H).

The conversion of the above linear decapeptide to the compond of formula 1 (R = H) is accomplished conveniently and efficiently by first subjecting the last-mentioned linear decapeptide to the action of the iodine, preferably in the presence of methanol or acetic acid [as described previously for the preparation of the cyclic undecapeptide derivative in (a)], whereby removal of the sulfhydryl protecting group, i.e. Trt, and under (a). Alternatively, the linear reduced form is obtained by direct reduction of the above cyclic decapeptide of formula 1 (R = H) in the manner described under (a).

Finally, it will be apparent to those skilled in the art that: equivalent amino, hydroxy or thiol protecting groups, equivalent methods of coupling peptide fragments, and equivalent methods for removal of amino, hydroxy or thiol protecting groups, other than those disclosed herein can be used in the embodiments of this invention without departing from the scope and spirit of the invention. Such apparent alternatives are intended to be included within the scope of this invention.

The following flow diagram in which R is as defined in the first instance and Examples illustrate further this invention.

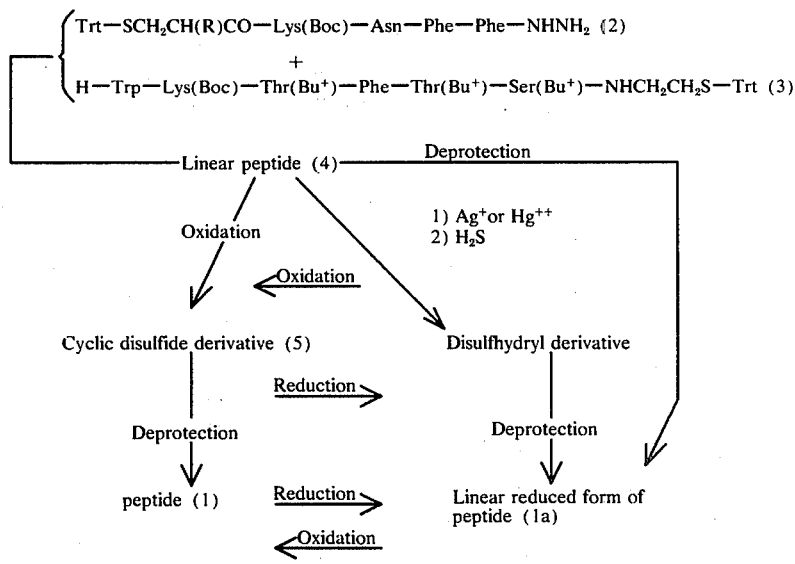

formation of the disulfide bridge occurs to give the corresponding cyclic disulfide derivative of formula (5) in which R is hydrogen,

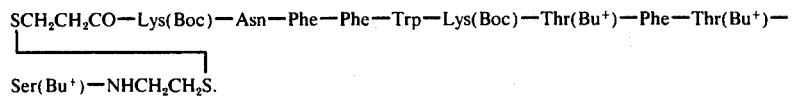

Subsequent treatment of the latter compound under moderately acidic conditions, preferably concentrated hydrochloric acid cooled to about 0° C [as described previously under (a)] removes the remaining protecting groups (i.e., Boc and Bu⁺) to give the cyclic decapeptide of formula 1 (R = H) having the structure,

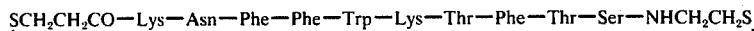

The linear reduced form of the latter cyclic decapeptide is obtained preferentially by removal of the protecting groups from the aforementioned linear decapeptide of formula (4) in which R is hydrogen. Convenient conditions for this deprotection step comprise dissolving the linear decapeptide in concentrated hydrochloric acid in the manner previously described

EXAMPLE 1

Acetyl-(S-trityl)cysteinyl-(N -t-butoxycarbonyl)lysyl-asparaginylphenylalanyl-phenylalanine Methyl Ester, Ac-Cys(Trt)—Lys(Boc)—Asn—Phe—Phe—OMe A solution of p-nitrophenyl acetate [0.191 g, 1.05 mmole, prepared as described by F.D Chattaway, J. Chem. Soc., 2495 (1931)] in dimethylformamide (4ml) is added to a solution at 0° C of H—Cys(Trt)—Lys(Boc)—Asn—Phe—OMe.HOAc[0.750 g, 0.698 mmole, prepared as described by H.U. Immer et al., Helv. Chim. Acta., 57, 730 (1974)] and N-ethylmorpholine (0.1 ml). After stirring at 0° C for 24 hr, the solvent is evaporated under reduced pressure. The residue is dissolved in methanol (3 ml) and slowly added to diethyl ether (200 ml). The precipitate is collected and crystallized from ethanol to give the title compound; mp 219.5°–221° C, $[\alpha]_D^{25} = -21.6°$ (c = 1, dimethylformamide).

In the same manner by using the p-nitrophenyl esters of formic, propionic, butyric, isobutyric, pivalic, n-hexanoic, or benzoic acid instead of p-nitrophenyl acetate, the corresponding compounds of the above formula in which Ac is replaced by formyl, propionyl, n-butanoyl, isobutanoyl, pivaloyl, n-hexanoyl, or benzoyl are also obtained.

EXAMPLE 2

Acetyl-(S-trityl)cysteinyl-(N -t-butoxycarbonyl)lysyl-asparaginylphenylalanyl-phenylalanine Hydrazide, Ac—Cys(Trt)—Lys(Boc)—Asn—Phe—Phe—NHNH$_2$. (2, R = NHCOCH$_3$)

A solution of Ac-Cys(Trt)—Lys(Boc)—Asn—Phe—Phe—OMe (0.40 g, 0.379 mmole, described in Example 1) and hydrazine hydrate (0.37 ml, 7.58 mmole) in methanol (15 ml) is stirred at 0° C for 48 hr. The precipitate is collected and dried to give the title compound; mp 236°–237° C, $[\alpha]_D^{25} = -28.6°$ (c = 1, dimethylformamide).

In the same manner, by using the appropriate other starting materials described in Example 1, the corresponding compounds of formula (2) in which R is NHR$^1$ wherein R$^1$ is formyl, propionyl, n-butanoyl, isobutanoyl, pivaloyl, n-hexanoyl, or benzoyl are also obtained.

EXAMPLE 3

Acetyl-(S-trityl)cysteinyl-(N -t-butoxycarbonyl)lysyl-asparaginyl-phenylalanyl-phenylalanyl-tryptophyl-(N -t-butoxycarbonyl)lysyl-(O-t-butyl)threonyl-phenylalanyl-(O-t-butyl)threonyl-(O-t-butyl)seryl-2-tritylthioethylamide, Ac—Cys(Trt)—Lys(Boc)—Asn—Phe—Phe—Trp—Lys(Boc)—Thr(Bu$^+$)—Phe—Thr(Bu$^+$)—Ser(Bu$^+$)—NHCH$_2$CH$_2$S—Trt (4, R = NHCOCH$_3$)

A solution of Ac—Cys(Trt)—Lys(Boc)—Asn—Phe—Phe—NHNH$_2$ (2) (0.240 g, 0.227 mmole, described in Example 2) in dry dimethylformamide (2 ml) and dimethyl sulfoxide (1 ml) is cooled to −20° C. Hydrochloric acid in ethyl acetate (2.1 N, 0.273 mmole) is added followed by t-butyl nitrite (0.0312 ml, 0.273 mmole). The mixture is stirred for 15 min at −15° C. A solution of H—Trp—Lys(Boc)—Thr(Bu$^+$)—Phe—Thr(Bu$^+$)—Ser(Bu$^+$)NHCH$_2$CH$_2$S—Trt (3, 0.304 g, 0.227 mmole, prepared as described in the copending U.S. Patent Application S.N. 493,595; filed August 1, 1974) in dimethylformamide (3 ml) containing N-ethyldiisopropylamine (0.097 ml, 0.568 mmole), cooled to −15° C, is added dropwise to the above reaction mixture. The mixture is stirred at −15° C for one hr and at 25° C for 20 hr. The solvent is evaporated under reduced pressure. The residue is triturated with ice cold citric acid (1 N) solution, filtered, washed with water and dried over phosphorous pentoxide. Th solid residue is triturated with methanol, filtered and dried over phosphorous pentoxide to give the title compound, amino acid analysis: Lys, 1.82; Asp, 1.00; Ser, 0.76; Cysteic acid, 0.93; Thr, 1.87; Phe, 3.10.

In the same manner, but using the appropriate other starting materials of formula (2) described in Example 2, the corresponding compounds of formula (4) in which R is NHR$^1$ wherein R$^1$ is formyl, propionyl, n-butanoyl, isobutanoyl, pivaloyl, n-hexanoyl, or benzoyl are also obtained.

EXAMPLE 4

Cyclic disulfide of acetyl—cysteinyl—lysyl—asparaginyl—phenylalanyl—phenylalanyl—tryptophyl—lysyl—threonyl—phenylalanyl—threonyl—seryl—2—thioethylamide,

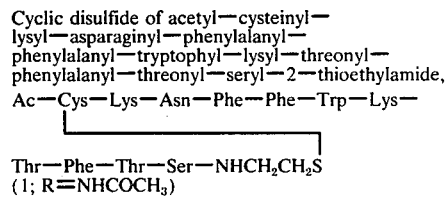

A solution of Ac—Cys(Trt)—Lys(Boc)—Asn—Phe—Phe—Trp—Lys(Boc)—Thr—(Bu$^+$)—Phe—Thr-(Bu$^+$)—Ser(Bu$^+$)—NHCH$_2$CH$_2$S—Trt (0.260 g, 0.110 mmole, described in Example 3) in acetic acid (61 ml) is slowly added to a stirred solution of iodine (0.278 g, 1.1 mmole) in methanol (56 ml) at 25° C. After completion of addition, the solution is stirred at 25° C for 1 hr. The solution is cooled to 0° C and a solution of 1 N sodium thiosulfate in water is slowly added to destroy the excess of iodine (colorless-solution). The solvent is evaporated under reduced pressure and the residue triturated with water. The precipitate is collected, washed with water and dried over phosphorus pentoxide to give the cyclic protected undecapeptide of the formula

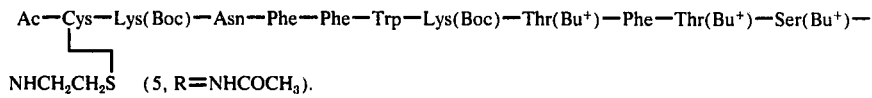

The latter cyclic peptide is vigorously stirred at 0° C under an atmosphere of nitrogen for 10 min in concentrated hydrochloric acid (9.1 ml). Acetic acid (119 ml) is added and the solution immediately lyophilized. The residue is dissolved in water and lyophilized. The residue is dissolved in the upper phase of the solvent system butanol-acetic acid-water (4:1:5) and applied to a column of a chemically modified cross-linked dextran (Sephadex G-25 M) prepared in the lower phase of the solvent system. The upper phase of the above solvent system is used to desorb the undecapeptide. The fractions containing the pure product are combined and evaporated under reduced pressure. The residue is triturated with diethyl ether, dissolved in 5% acetic acid and lyophilized to give the title compound as the acetic addition salt, U.V. (methanol): λ max 290 (ε 4990), 282 (ε 5455), 274 nm (ε 5095).

The latter compound in the form of the acetic acid addition salt is subjected to repeated lyophilization from the water to give the title compound in the form of the free base, amino acid analysis: Lys, 1.93; Asp, 1.00; Ser, 0.84; Cysteic acid, 0.80; Thr, 1.84; Phe, 2.97.

In the same manner, by using the appropriate other starting materials of formula (4) described in Example 3, the corresponding compounds of formulae (5) and (1) in which R is NHR¹ wherein R¹ is formyl, propionyl, n-butanoyl, isobutanoyl, pivaloyl, n-hexanoyl or benzoyl are also obtained.

EXAMPLE 5

3-Tritylthiopropionic acid Pentachlorophenyl Ester (Trt-SCH₂CH₂COOPcp)

3-Tritylthiopropionic acid [1.0 g, 2.87 mmoles, described by R.C. Hiskey and M.A. Harpold, J. Org. Chem., 33, 559 (1968)] is dissolved in dry tetrahydrofuran (25 ml) and pentachlorophenol (0.765 g, 2.87 mmoles) is added. The mixture is cooled to 0° C, dicyclohexylcarbodiimide (0.596 g, 2.87 mmoles) is added and the reaction is stirred for 1 hr at 0° C and 1 hr at 25° C. The reaction mixture is then cooled to 0° C, filtered and the filtrate is evaporated under reduced pressure. The residue is crystallized from ethyl acetate to give the title compound mp 154°–156° C.

EXAMPLE 6

3-Tritylthiopropionyl-(N -t-butoxycarbonyl)lysyl-asparaginyl-phenylalanyl-phenylalanine Methyl Ester, Trt-SCH₂CH₂CO-Lys(Boc)-Asn-Phe-Phe-OMe A solution of 3-tritylthiopropionic acid pentachlorophenyl ester (0.597 g, 1 mmole, described in Example 5), H-Lys(Boc)-Asn-Phe-Phe-OMe.HOAc [1 mmole, prepared as described by H.U. Immer et al., Helv. Chim. Acta., 57, 730 (1974)] and triethylamine (0.14 ml, 1 mmole) is stirred at 25° C for 3 days. The solvent is evaporated under reduced pressure. The residue is triturated with ice cold 1N citric acid solution, filtered, washed with water and dried over potassium hydroxide. The solid is crystallized from methanol to give the title compound, mp 215°–220° C.

EXAMPLE 7

3-Tritylthiopropionyl-(N -t-butoxycarbonyl)lysyl-asparaginyl-phenylalanylphenylalanine Hydrazide, Trt—SCH₂CH₂CO—Lys(Boc)—Asn—Phe—Phe—NHNH₂ (2, R = H)

A solution of Trt-SCH₂CH₂CO-Lys(Boc)—Asn—Phe—Phe—OMe (0.900 g, 0.9 mmole, described in Example 6) and hydrazine hydrate (1 ml) in dimethylformamide (20 ml) is stirred at 25° C for 20 hr. The solvent is evaporated under reduced pressure. The residue is triturated with cold water, filtered, washed with water and dried to give the title compound, mp 225°–235° C.

EXAMPLE 8

3-Tritylthiopropionyl-(N -t-butoxycarbonyl)lysyl-asparaginyl-phenylalanyl-phenylalanyl-tryptophyl-(N -t-butoxycarbonyl)lysyl-(O-t-butyl)threonyl-phenylalanyl-(O-t-butyl)threonyl-(O-t-butyl)seryl-2-tritylthioethylamide,
Trt—SCH₂CH₂CO—Lys(Boc)—Asn—Phe—Phe—Trp—Lys(Boc)—Thr(Bu⁺)—Phe—Thr(Bu⁺)—Ser—(-Bu⁺)—NHCH₂CH₂S—Trt (4, R = H)

A solution of Trt—SCH₂CH₂CO—Lys(Boc)—Asn—Phe—Phe—NHNH₂ (0.500 g, 0.5 mmole, described in Example 7) in dimethyl sulfoxide (5 ml) and dimethylformamide (20 ml) is cooled to −20° C. A solution of hydrochloric acid in ethyl acetate (1.4 N, 0.895 ml) is added followed by t-butyl nitrite (0.069 ml, 0.6 mmole). The mixture stirred at −15° C for 15 min and a solution, cooled to −15° C, of H—Trp—Lys(Boc)—Thr(Bu⁺)—Phe—Thr(Bu⁺)—Ser(Bu⁺·)—NHCH₂CH₂S—Trt (0.670 g, 0.5 mmole, prepared as described in the copending U.S. patent application Ser. No. 493,595; filed Aug. 1, 1974) and N-ethyldiisopropylamine (0.214 ml, 1.25 mmole) in dimethylformamide (10 ml) is added. The reaction mixture is stirred at −15° C for 1 hr and at 25° C for 20 hr and evaporated under reduced pressure. The residue is triturated with ice cold 1N citric acid solution, filtered, washed with water and dried over phosphorous pentoxide. The solid is triturated with cold methanol and dried to give the title compound, amino acid analysis: Lys, 1.99; Asp, 1.15; Thr, 1.73; Ser, 0.67; Phe, 3.00.

EXAMPLE 9

Cyclic disulfide of 3—thiopropionyl—lysyl—asparaginyl—phenylalanyl—phenyl—alanyl—tryptophyl—lysyl—threonyl—phenylalanyl—threonyl—seryl—2—thioethyl—amide (SCH₂CH₂CO—Lys—Asn—Phe—Phe—Trp—
|_____|
Lys—Thr—Phe—Thr—Ser—NHCH₂CH₂S)
(1; R = H)

A solution of Trt—SCH₂CH₂CO—Lys(Boc)—Asn—Phe—Phe—Trp—Lys(Boc)—Thr(Bu⁺)—Phe—Thr(Bu⁺)—Ser(Bu⁺)—NHCH₂CH₂S—Trt (0.500 g, 0.216 mmole, described in Example 8) in acetic acid (100 ml) is slowly added to a stirred solution of iodine (0.547 g, 2.16 mmoles) in methanol (110 ml) at 25° C. After completion of addition, the solution is stirred at 25° C for 1 hr. The solution is cooled to 0° C and a solution of 1 N sodium thiosulfate in water is slowly added to destroy the excess iodine (colorless solution). The solvent is evaporated under reduced pressure and the residue triturated with water. The precipitate is collected, washed several times with water and dried over phosphorous pentoxide to give the cyclic protected decapeptide of formula

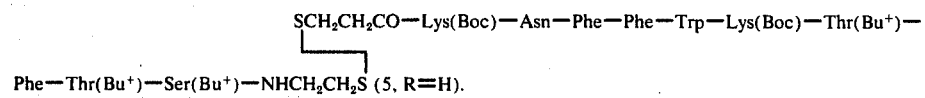

Phe—Thr(Bu⁺)—Ser(Bu⁺)—NHCH₂CH₂S (5, R=H).

The latter cyclic decapeptide is vigorously stirred at 0° C under an atmosphere of nitrogen for 10 min in concentrated hydrochloric acid (18 ml). Acetic acid (200 ml) is added and the solution immediately lyophilized. The residue is dissolved in water and lyophilized. The residue is dissolved in the upper phase of the solvent system butanolacetic acid-water (4:1:5) and applied to a column of a chemically modified cross-linked dextran (Sephadex G-25 M) prepared in the lower phase of the solvent system. The upper phase of the above solvent system is used to desorb the decapeptide. The fractions containing the pure product are combined and evaporated under reduced pressure. The residue is dissolved in 5% acetic acid and lyophilized to give the title compound as the acetic acid addition salt, U.V. (methanol): λ max 290 (ε 4920), 282 nm (ε 5390).

The latter compound in the form of the acetic acid addition salt is subjected to repeated lyophilization from water to give the title compound in the form of the free base, amino acid analysis: Lys, 1.97; Asp, 1.00; Thr, 1.64; Ser, 0.65; Phe, 2.94.

We claim:

1. A process for preparing a peptide of formula 1

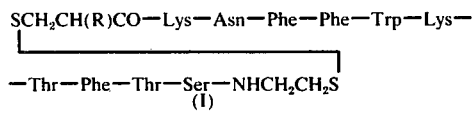

in which R is hydrogen or NHR$^1$ wherein R$^1$ is a lower aliphatic acyl having from 1 - 6 carbon atoms, or benzoyl, which comprises: reacting a peptide hydrazide of formula (2) Trt—SCH$_2$CH(R)CO—Lys—(Boc)—Asn—Phe—Phe—NHNH$_2$ in which R is as defined herein with a reagent which furnishes nitrous acid in situ in the presence of a strong acid to convert said peptide hydrazide to the corresponding peptide azide and reacting said azide with a hexapeptide of formula (3) H—Trp—Lys(Boc)—Thr(B$^+$)—Phe—Thr(Bu$^+$)—Ser(Bu$^+$)—NHCH$_2$CH$_2$S—Trt to obtain the linear peptide of formula (4) Trt—SCH$_2$CH(R)CO—Lys(Boc)—Asn—Phe—Phe—Trp—Lys—(Boc)—Thr(Bu$^+$)—Phe—Thr(Bu$^+$)—Ser(Bu$^+$)—NHCH$_2$CH$_2$S—Trt in which R is as defined herein, followed by oxidizing said linear peptide with iodine or thiocyanogen to obtain the corresponding cyclic disulfide derivative of formula (5)

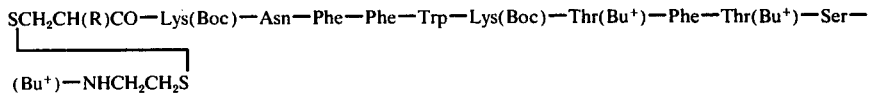

in which R is as defined herein and subsequently removing all remaining protecting groups under moderately acidic conditions to obtain the corresponding peptide of formula 1; or followed by subjecting said linear peptide (4) to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative by treatment with hydrogen sulfide, oxidizing said last-named derivative by treatment with oxygen, 1,2-diiodoethane, sodium or potassium ferricyanide or iodine to obtain the corresponding cyclic disulfide derivative (5) and removing the remaining protecting groups under moderately acidic conditions to obtain the desired peptide of formula 1.

2. A process as claimed in claim 1 in which the peptide hydrazide of formula (2) Trt—SCH$_2$CH(R)CO—Lys(Boc)—Asn—Phe—Phe—NHNH$_2$ in which R is NHR$^1$ wherein R$_1$ is as defined in claim 1 is prepared by acylation of the pentapeptide of formula H—Cys(Trt)—Lys(Boc)—Asn—Phe—Phe—OMe to obtain the corresponding pentapeptide of formula R$^1$ Cys(Trt)—Lys(Boc)—Asn—Phe—Phe—OMe followed by reacting said last-named compound with hydrazine hydrate and isolating said peptide hydrazide.

3. A process as claimed in claim 1 in which the peptide hydrazide of formula (2) Trt—SCH$_2$CH(R)CO—Lys(Boc)—Asn—Phe—Phe—NHNH$_2$ in which R is hydrogen is prepared by reacting an activated ester of 3-tritylthiopropionic acid with the tetrapeptide of formula H—Lys(Boc)—Asn—Phe—Phe—OMe to obtain the tetrapeptide of formula Trt—SCH$_2$CH$_2$CO—Lys(Boc)—Asn—Phe—Phe—OMe, followed by reacting said last-named compound with hydrazine hydrate and isolating said peptide hydrazide.

4. A process as claimed in claim 1 in which the linear peptide (4) as defined therein is subjected to moderately acid conditions to obtain the corresponding compound of formula 1a HSCH$_2$CH(R)CO—Lys—Asn—Phe—Phe—Trp—Lys—Thr—Phe—Thr—Ser—NHCH$_2$CH$_2$SH in which R is as defined therein.

5. A process as claimed in claim 1 in which the corresponding disulfhydryl derivative as defined therein is subjected to moderately acidic conditions to obtain the compound of formula 1a HSCH$_2$CH(R)CO—Lys—Asn—Phe—Phe—Trp—Lys—Thr—Phe—Thr—Ser—NHCH$_2$CH$_2$SH in which R is as defined therein.

6. The process as claimed in claim 1 wherein said linear peptide (4) is subjected to treatment with iodine in the presence of a lower alkanol or acetic acid to obtain the corresponding cyclic disulfide derivative (5).

7. The process as claimed in claim 1 wherein said linear peptide (4) is subjected to treatment with iodine at from about 0° to 30° C for about 30 to 180 minutes in a lower alkanol or acetic acid to obtain the corresponding cyclic disulfide derivative.

8. A compound of the formula 1

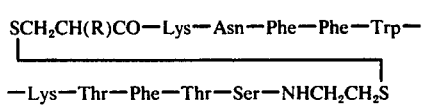

in which R is hydrogen or NHR$^1$ wherein R$^1$ is a lower aliphatic acyl having from 1 – 6 carbon atoms, or benzoyl.

9. The compound of claim 8 in which R is hydrogen.

10. The compound of claim 8 in which R is NHCOCH$_3$.

11. A compound of the formula 1a

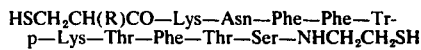

in which R is hydrogen or NHR$^1$ wherein R$^1$ is a lower aliphatic acyl having from 1–6 carbon atoms, or benzoyl.

12. The compound of claim 11 in which R is hydrogen.

13. The compound of claim 11 in which R is NHCOCH$_3$.

14. A compound of the formula 5

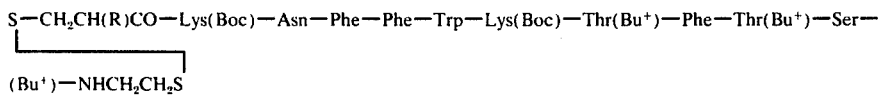

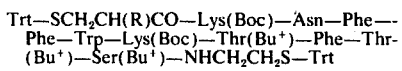

in which R is hydrogen or NHR$^1$ wherein R$^1$ is a lower aliphatic acyl having from 1–6 carbon atoms, or benzoyl.

15. A compound of claim 14 in which R is hydrogen.

16. The compound of claim 14 in which R is NHCOCH$_3$.

17. A compound of the formula 4

Trt—SCH$_2$CH(R)CO—Lys(Boc)—Asn—Phe—
   Phe—Trp—Lys(Boc)—Thr(Bu$^+$)—Phe—Thr-
   (Bu$^+$)—Ser(Bu$^+$)—NHCH$_2$CH$_2$S—Trt in which R is NHR$^1$ wherein R$^1$ is a lower aliphatic acyl having from 1–6 carbon atoms, or benzoyl.

18. The compound of claim 17 in which R is hydrogen.

19. The compound of claim 17 in which R is NHCOCH$_3$.

20. A compound of the formula Trt—SCH$_2$CH(R)CO—Lys(Boc)—Asn—Phe—Phe—NHNH$_2$ in which R is hydrogen or NHR$^1$ wherein R$^1$ is a lower aliphatic acyl having from 1–6 carbon atoms, or benzoyl.

21. The compound of claim 20 in which R is hydrogen.

22. The compound of claim 20 in which R is NHCOCH$_3$.

23. A compound of the formula CH$_3$CO—Cys(Trt)—Lys(Boc)—Asn—Phe—Phe—OMe.

24. A compound of the formula Trt—SCH$_2$CH$_2$CO—Lys(Boc)—Asn—Phe—Phe—OMe.

25. A pharmaceutical composition which comprises a compound of the formula 1 as claimed in claim 8, and a pharmaceutically acceptable liquid or solid carrier therefor.

26. A method of treating acromegaly in mammals, which comprises administering to said mammal an effective dose of a compound of the formula 1 as claimed in claim 8.

27. A method of treating diabetes in mammals which comprises administering to said mammal an effective dose of a compound of the formula 1 as claimed in claim 8.

28. A pharmaceutical composition which comprises a compound of the formula 1a as claimed in claim 11, and a pharmaceutically acceptable liquid or solid carrier therefor.

29. A method of treating acromegaly in mammals, which comprises administering to said mammal an effective dose of a compound of the formula 1a as claimed in claim 11.

30. A method of treating diabetes in mammals which comprises administering to said mammal an effective dose of a compound of the formula 1a as claimed in claim 11.

31. A pharmaceutically acceptable acid addition salt of the compound of formula 1 as claimed in claim 8.

32. The acid addition salt of claim 31 in which the acid is hydrochloric acid.

33. The acid addition salt of claim 32 in which the acid is acetic acid.

34. A pharmaceutically acceptable acid addition salt of the compound of formula 1a as claimed in claim 11.

35. The acid addition salt of claim 34 in which the acid is hydrochloric acid.

36. The acid addition salt of claim 34 in which the acid is acetic acid.

* * * * *

UNITED STATES PATENT AND TRADEMARK OFFICE
CERTIFICATE OF CORRECTION

PATENT NO. : 4,020,157
DATED : April 26, 1977
INVENTOR(S) : Abraham et al

It is certified that error appears in the above-identified patent and that said Letters Patent are hereby corrected as shown below:

Column 3, line 35, for "HSCH$_2$CH(R)CO-Lys-Asn-Phe-Trp-Lys-" read —HSCH$_2$CH(R)CO-Lys-Asn-Phe-Phe-Trp-Lys- —:

Column 9 line 36, for "Trp-Lys-(Boc)-Thr(Bu$^+$)-Ser(Bu$^+$)-NHCH$_2$CH$_2$S-Trt" read — Trp-Lys(Boc)-Thr(Bu$^t$)-Phe-Thr(Bu$^t$)-Ser(Bu$^t$)-NHCH$_2$CH$_2$S Trt—;

Column 9, line 45, for "unecapeptide" read —undecapeptide—;

Column 12, line 44, for "H-Trp-Lys(Boc)-Thr-" read —H-Trp-Lys(Boc)-Thr(Bu$^t$)-Phe-Thr- —;

Column 15, line 15, for "(N -t-butoxycarbonyl)" read —(N$^\epsilon$-t-butoxycarbonyl)—;

Column 15, line 34, for "(N -t-butoxycarbonyl)" read —(N$^\epsilon$-t-butoxycarbonyl)—;

Column 15, line 42, for "(N t-butoxycarbonyl)" read —(N$^\epsilon$-t-butoxycarbonyl)—;

UNITED STATES PATENT AND TRADEMARK OFFICE
CERTIFICATE OF CORRECTION

PATENT NO. : 4,020,157

DATED : April 26, 1977

INVENTOR(S) : Abraham et al

It is certified that error appears in the above-identified patent and that said Letters Patent are hereby corrected as shown below:

Column 17, line 22, for "(N -t-butoxycarbonyl)" read --($N^\varepsilon$-t-butoxycarbonyl)--;

Column 17, line 38, for "(N -t-butoxycarbonyl)" read --($N^\varepsilon$-t-butoxycarbonyl)--;

Column 17, line 58, for "(N -t-butoxycarbonyl)" read --($N^{\varepsilon}$-t-butoxycarbonyl)--;

Column 17, line 60, for "(N -t-butoxycarbonyl)" read --($N^\varepsilon$-t-butoxycarbonyl)--;

Column 12, line 50, for "Lys(Boc)-Thr($Bu^+$)" read --Lys(Boc)-Thr($Bu^t$)-Phe-Thr($Bu^t$ --

Claim 1, Column 19, line 26, for "p-Lys(Boc)-Thr($B^+$)" read --p-Lys(Boc)-Thr($Bu^t$)--

Signed and Sealed this

Twenty-second Day of May 1979

[SEAL]

Attest:

RUTH C. MASON
Attesting Officer

DONALD W. BANNER
Commissioner of Patents and Trademarks